US005625031A

United States Patent [19]
Webster et al.

[11] Patent Number: 5,625,031
[45] Date of Patent: Apr. 29, 1997

[54] PEPTIDE INHIBITORS OF THE $P33^{CDK2}$ AND $P34^{CDC2}$ CELL CYCLE REGULATORY KINASES AND HUMAN PAPILLOMAVIRUS E7 ONCOPROTEIN

[75] Inventors: Kevin R. Webster, Newton, Pa.; Kevin G. Coleman, Hopewell, N.J.

[73] Assignee: Bristol-Myers Squibb Company, New York, N.Y.

[21] Appl. No.: 193,977

[22] Filed: Feb. 8, 1994

[51] Int. Cl.$^6$ .............................. C07K 7/00; C07K 7/06; C07K 7/08; C07K 14/00
[52] U.S. Cl. ..................... 530/300; 530/326; 530/327; 530/328; 530/329; 530/330
[58] Field of Search ................................. 530/300, 350; 514/12, 13, 14, 15, 16, 17

[56] References Cited

FOREIGN PATENT DOCUMENTS

WO93/06123  4/1993  WIPO .

OTHER PUBLICATIONS

Bignon et al., Genes & Development 7:1654–1662 (1993).
Freidman, Cancer 70:1810–1817 (1992).
Parker et al, Proc. Natl. Acad. Sci. USA 89:2917–2921 (1992).
Bandara et al., Cyclin A and the retinoblastoma gene product complex with a common transcription factor, (1991) Nature 352:249–252.
Chelappan et al., The E2F transcription factor is a cellular target for the RB protein, (1991) Cell 65:1053–1061.
Cross et al., Simple and Complex cell cycles, (1989) Ann. Rev. Cell Biol. 5:341–395.
Devoto et al., A cyclin A–Protein kinase complex possesses sequence-specific DNA binding activity:$p33^{cdk2}$ is a component of the E2F–cyclin A complex, (1992) Cell 68:167–176.
Draetta et al., cdc2 protein kinase is complexed with both cyclin A dn B: Evidence for proteolytic inactivation of MPF, (1989) Cell 56:829–838.
Draetta, Cell cycle control in eukaryotes: Molecular mechanisms of cdc2 activation, (1990) TIBS 15:378–383.
Draetta et al., Activation of cdc2 protein kinase during mitosis in human cells: Cell cycle–dependent phosphorylation and subunit rearrangement, (1988), Cell 54:17–26.
Dyson et al., The human papilloma virus–16 E7 oncoprotein is able to bind to the retinoblastoma gene product, (1989) Science 243:934–937.
Elledge et al., CDK2 encodes a 33–kDa cyclin A–associated protein kinase and is expressed before CDC2 in the cell cycle, (1992) Proc. Natl. Acad. Sci. USA 89:2907–2911.
Ewen et al., Interaction of p107 with cyclin A independent of complex formation with viral oncoproteins, (1992) Science 255:85–87.
Ewen et al., Molecular cloning, chromosomal mapping, and expression of the cDNA for p107, a retinoblastoma gene product–related protein, (1991) Cell 66:1155–1164.

Faha et al., Interaction between human cyclin A and adenovirus E1A–associated p107 protein, (1992) Science 255: 87–90.
Furukawa et al., CDC2 gene expression at the $G_1$ to S transition in human T lymphocytes, (1990) Science 250:805–808.
Gage et al., The E7 proteins of the nonnoncogenic human papillomavirus type 6b (HPV–6b) and of the oncogenic HPV–16 differ in retinoblastoma protein binding and other properties, (1990) J. Virol. 64:723–730.
Giordano et al., A 60 kd CDC2–associated polypeptide complexes with the E1A proteins in adenovirus–infected cells, (1989) Cell 981–990.
Gu et al., Inhibition of CDK2 activity in vivo by an associated 20K regulatory subunit, (1993) Nature 366:707–710.
Harper et al., The p21 CDK–interacting protein Cip1 is a potent inhibitor of G1 cyclin–dependent kinases, (1993) Cell 75:805–816.
Horowitz et al., Point mutational inactivation of the retinoblastoma antioncogene, (1989) Science 243:937–940.
Hu et al., The regions of the retinoblastoma protein needed for binding to adenovirus E1A or SV40 latge T antigen are common sites for mutations, (1990) EMBO J. 9:1147–1155.
Hunt, T., Maturation promoting factor, cyclin and the control of M–phase, (1989) Curr. Opinion Cell Biol. 1:268–274.
Kaye et al., A single amino acid substitution results in a retinoblastoma protein defective in phosphorylation and oncoprotein binding, (1990) Proc. Natl. Acad. Sci. USA 87:6922–6926.
Labbé et al., Purification of MPF from starfish: Identification as the H1 histone kinase $p34^{cdc2}$ and a possible mechanism for its periodic activation, (1988) Cell 57:253–263.
Lee et al., Cell cycle control genes in fission yeast and mammalian cells, (1988) Trends Genet. 4:287–90.
Lew et al., Isolation of three novel human cyclins by rescue of G1 cyclin (Cln) function in yeast, (1991) Cell 66:1197–1206.
Motokura et al., A novel cyclin encoded by a bc/1–linked candidate oncogene, (1991) Nature 350:512–515.
Mundryi et al., Cell cycle regulation of the E2F transcription factor involves an interaction with cyclin A, (1991) Cell 65:1243–1253.
Murray et al., The role of cyclin synthesis and degradation in the control maturation promoting factor activity, (1989) Nature 339:280–286.
Nurse, Universial controlmechanism regulating onset of M–phase, (1990) Nature 344:503–508.

(List continued on next page.)

Primary Examiner—Robert A. Wax
Assistant Examiner—Eric Grimes
Attorney, Agent, or Firm—Reed & Robins

[57] ABSTRACT

Novel peptide and peptide mimetic ligands which act as inhibitors of $p34^{cdc2}$ kinase, $p33^{cdk2}$ kinase and human papillomavirus transforming protein E7 (HPV E7) are disclosed. The inhibitors are derived from the binding domains of a retinoblastoma tumor suppressor protein (Rb), p107 and a cyclin.

5 Claims, 4 Drawing Sheets

OTHER PUBLICATIONS

Pines et al., Human cyclin A is adenovirus E1A–associated protein p60 and behaves differently from cyclin B, (1990) *Nature* 346:760–763.

Pines et al., Isolation of a human cyclin cDNA: Evidence for cyclin mRNA and protein regulation in the cell cycle and for interactions with p34$^{cdc2}$, (1989) *Cell* 58:833–846.

Rosenblatt et al., Human cyclin–dependent kinase 2 is activated furing the S and $G_2$ phases of the cell cycle and associated with cyclin A, (1992) *Proc. Natl. Acad. Sci. USA* 89:2824–2828.

Serrano et al., A new regulatory motif in cell–cycle control causing specific inhibition of cyclin D/CDK4, (1993) *Nature* 366:704–707.

Shirodkar et al., The transcription factor E2f interacts with the retinoblastoma product and a p107–cyclin A complex in a cell cycle–regulated manner, (1992) *Cell* 68:157–166.

Solomon et al., Cyclin activation of p34$^{cdc2}$, (1990) *Cell* 63:1013–1024.

Tsai et al., Isolation of the human cdk2 gene that encodes the cyclin A– and adenovirus E1A–associated p33 kinase, (1991) *Nature* 353:174–177.

Wang et al., Hepatitis B virus integration in a cyclin A gene in a hepatocellular carcinoma, (1990) *Nature* 343:555–557.

Whyte et al., Association between an oncogene and an anti–oncogene: the adenovirus E1A proteins bind to the retinoblastoma gene product, (1988) *Nature* 334:124–129.

Xiong et al., p21 is a universial inhibitor of cyclin kinases, (1993) *Nature* 366:701–704.

Xiong et al., Subunit rearrangement of the cyclin–dependent kinases in associated with cellular transformation, (1993) *Genes and Development* 7:1572–1583.

FIG. 1

PEPTIDE INHIBITORS OF THE P33$^{CDK2}$ AND P34$^{CDC2}$ CELL CYCLE REGULATORY KINASES AND HUMAN PAPILLOMAVIRUS E7 ONCOPROTEIN

TECHNICAL FIELD

The present invention relates generally to peptide inhibitors of cell growth and proliferation. More particularly, the invention relates to ligands which bind to p34$^{cdc2}$/p33$^{cdk2}$ kinase and inhibit the activity thereof, and which inhibit the specific interaction between retinoblastoma tumor suppressor protein and human papillomavirus transforming protein E7.

BACKGROUND OF THE INVENTION

Cancer cells are characterized by their ability to proliferate in a continuous, uncontrolled fashion. It is now clear that primary cell cycle regulators must be circumvented or directly involved in oncogenesis in order for this to occur.

Cell cycle regulation occurs at the boundaries of the $G_1$/S and $G_2$/M phases, two major transition points of the cell cycle. A key regulator of these transitions is p34$^{cdc2}$ kinase which is known to phosphorylate a number of proteins including histone H1, DNA polymerase α, RNA polymerase II, retinoblastoma tumor suppressor protein (Rb), p53, nucleolin, cAb1, SV40 large T antigen and lamin A. For example, p34$^{cdc2}$ kinase activity is required for entry of cells into mitosis, i.e., for passage from the $G_2$ phase of the cell cycle into the M phase. (Lee et al. (1988) *Trends Genet.* 4:289–90; Dunphy et al. (1988) *Cell* 54:423–431; Gautier et al. (1988) *Cell* 54:433–439; see, for review, Cross et al. (1989) *Ann. Rev. Cell Biol.* 5:341–395; Hunt (1989) *Curr. Opinion Cell Biol.* 1:268–274; Nurse (1990) *Nature* 344:503–508).

The activity of p34$^{cdc2}$ kinase is, in turn, regulated by both protein:protein interactions and post-translational modifications. Thus, blockage of either of these mechanisms leads to arrest of the mammalian cell cycle. For example, microinjection of p34$^{cdc2}$ antibodies into serum-stimulated rat fibroblasts causes cells to arrest in $G_2$ and treatment of activated T lymphocytes with p34$^{cdc2}$ anti-sense oligodeoxynucleotides inhibits DNA synthesis (Furukawa et al. (1990) *Science* 250:805–808; Riabowol et al. (1989) *Cell* 57:393–401). Injection of suc1 protein (a ligand of p34$^{cdc2}$) into HeLa cells arrests cell growth, presumably by disrupting normal p34$^{cdc2}$ protein:protein interactions (Draetta (1990) *TIBS* 15:378–383). In addition, inhibition of the cdc25 phosphatase with specific antibodies blocks the post-translational modification of p34$^{cdc2}$ and leads to HeLa cell death (Galaktionov et al. (1991) *Cell* 67:1181–1194).

Rb, p107 protein and the cyclin (cyc) protein family have been shown to associate with p34$^{cdc2}$ (and its homolog p33$^{cdk2}$) (Pines et al. (1990) *Nature* 346:760–763; Tsai et al. (1991) *Nature* 353:174–177; Giordano et al. (1989) *Cell* 58:981–990); the E2F transcription factor; the adenovirus E1A protein; and the human papillomavirus transforming protein E7 (Whyte et al. (1988) *Nature* 334:124–129; Chelappan et al. (1991) *Cell* 65:1053–1061; Bandara et al. (1991) *Nature* 352:249–252; Mundryj et al. (1991) *Cell* 65:1243–1253; Pines et al. (1990), supra; Tsai et al. (1991), supra; Giordano et al. (1989), supra; Shirodkar et al. (1992) *Cell* 68:157–166; Devoto et al. (1992) *Cell* 68:157–166; DeCaprio et al. (1988) *Cell* 54:275–283; Dyson et al. (1989) *Science* 243:934–937; Gage et al. (1990) *J. Virol.* 64:723–730). The binding of cyclins to p34$^{cdc2}$ or p33$^{cdk2}$ is required for kinase activity (Solomon et al. (1990) *Cell* 63:1013–1024; Pines et al. (1990), supra; Tsai et al. (1991), supra; Giordano et al. (1989), supra).

The functional domains of the Rb and p107 proteins have been mapped through both genetic and biochemical means. (Hu et al. (1990) *EMBO J.* 9:1147–1155; Ewen et al. (1991) *Cell* 66:1155–1164; Ewen et al. (1992) *Science* 255:85–87). An approximately 400 amino acid fragment of Rb and p107, termed the Rb pocket, is responsible for association of these proteins with the DNA tumor virus oncoproteins and cellular ligands. Within this domain are six regions of extensive sequence similarity between Rb and p107. (Ewen et al. (1991), supra). Likewise, the cyclins share a large region of sequence similarity spanning approximately 87 amino acids, which has been designated the "cyclin box." (Pines et al. (1989) *Cell* 58:833–846) This domain is thought to play a role in protein:protein interactions and it has been shown that deletion of sequences amino-terminal to this domain do not affect cyclin function. (Murray et al. (1989) *Nature* 339:280–286; Lew et al. (1991) Cell 66:1197–1206).

p34$^{cdc2}$ protein:protein interactions are altered in human tumors. For example, the gene encoding the cofactor cyclin A is disrupted in hepatocellular carcinoma (Wang et al. (1990) *Nature* 343:555–557). Also, recent data have demonstrated that cyclin D1 (PRAD1) is within the bcl-1 locus and is rearranged in parathyroid tumors and some B cell leukemias (de Boer et al. (1993) *Cancer Res.* 53:4148–4152; Motokura et al. (1991) *Nature* 350:512–515). In addition, the bcl-1 locus is frequently amplified in breast carcinoma and cyclin D1 is overexpressed in mouse skin carcinoma (Lammie et al. (1991) *Oncogene* 6:439–444; Bianchi et al. (1993) *Oncogene* 8:1127–1133; Buckley et al. (1993) *Oncogene* 8:2127–2133). Furthermore, the subunits of the cdk kinases are rearranged in transformed cells when compared to their normal counterpart (Xiong et al. (1993) *Genes and Development* 7:1572–1583). This is the result of the loss or underexpression of waf1/cip1 protein, which is normally a repressor of cdk kinase activities, and is regulated by the p53 tumor suppressor protein (Xiong et al. (1993) *Nature* 366:701–704; Serrano et al. (1993) *Nature* 366:704–707; Gu et al. (1993) *Nature* 366:707–710; Harper et al. (1993) *Cell* 75:805–816; El-Deiry et al. (1993) *Cell* 75:817–825). These data clearly implicate the alteration of p34$^{cdc2}$ kinase activity in oncogenesis.

Accordingly, inhibitors of p34$^{cdc2}$ activity would be useful in the regulation and control of the continuous, proliferative growth of cancerous cells.

SUMMARY OF THE INVENTION

The present invention provides for ligands that inhibit the course of cellular proliferation by preventing progression through the $G_1$/S or $G_2$/M boundaries by inhibition of p34$^{cdc2}$ kinase activity. The ligands are useful as modulators of p34$^{cdc2}$ kinase-mediated cell growth and proliferation and, thus, as agents for studying the mechanisms by which cancer cells proliferate in a continuous fashion and as agents for ameliorating tumors associated with disruption of genes which code for essential cyclins, for example, hepatocellular carcinomas, parathyroid tumors, various B cell leukemias and breast carcinomas or tumors which contain a p53 mutation or loss of waf1/cip1.

Accordingly, in one embodiment, the invention is directed to an inhibitor of p34$^{cdc2}$ cell cycle regulatory kinase activity, or an inhibitor of the kinase activity of a homolog thereof, wherein the inhibitor is derived from a p34$^{cdc2}$ binding domain of a protein selected from the group consisting of an Rb, p107 and a cyclin.

3

In preferred embodiments, the inhibitor is a peptide including the amino acid sequence LCAFYIMAK [SEQ ID NO: 2], a peptide including the amino acid sequence MCSMYGICK [SEQ ID NO: 2], a peptide including the amino acid sequence CAFYI [SEQ ID NO: 3], or substitutions of these sequences which retain inhibitory activity.

In a further embodiment, the invention is directed to an inhibitor of human papillomavirus E7 protein, wherein the inhibitor is derived from a $p34^{cdc2}$ binding domain of a protein selected from the group consisting of an Rb, p107 and a cyclin.

In another preferred embodiment, the invention is directed to a complex comprising:

(a) $p34^{cdc2}$ or a homolog thereof; and (b) an inhibitor of $p34^{cdc2}$ cell cycle regulatory kinase activity, wherein the inhibitor is derived from a $p34^{cdc2}$ binding domain of a protein selected from the group consisting of an Rb, p107 and a cyclin, and wherein the complex substantially lacks kinase activity.

In another embodiment, the invention is directed to a complex comprising:

(a) human papillomavirus E7 protein; and (b) an inhibitor of human papillomavirus E7 protein, wherein the inhibitor is derived from a $p34^{cdc2}$ binding domain of a protein selected from the group consisting of an Rb, p107 and a cyclin.

In a further embodiment, the invention is directed to a method of inhibiting $p34^{cdc2}$ cell cycle regulatory kinase activity, or the kinase activity of a homolog thereof, comprising providing a $p34^{cdc2}$ inhibitor as described above and contacting $p34^{cdc2}$ or the homolog thereof with an inhibiting amount thereof.

In an additional embodiment, the invention is directed to a method of inhibiting human papillomavirus E7 activity, comprising providing a human papillomavirus E7 inhibitor and contacting human papillomavirus E7 with an inhibiting amount thereof.

These and other embodiments of the subject invention will readily occur to those of ordinary skill in the art in view of the disclosure herein.

BRIEF DESCRIPTION OF THE FIGURES

FIG. 1 depicts a comparison of the amino acid sequences of various $p34^{cdc2}$ binding proteins including cyclins A, B1, C, D and E, p107 and Rb [SEQ ID NOS: 4–10]. Gaps were introduced to maximize homology, and are represented by dashes. Amino acids are represented by their single letter code. Boxes indicate identical amino acids or conservative changes. The stipled cylinder represents the α-helix II region.

4

DETAILED DESCRIPTION

Figure 2:
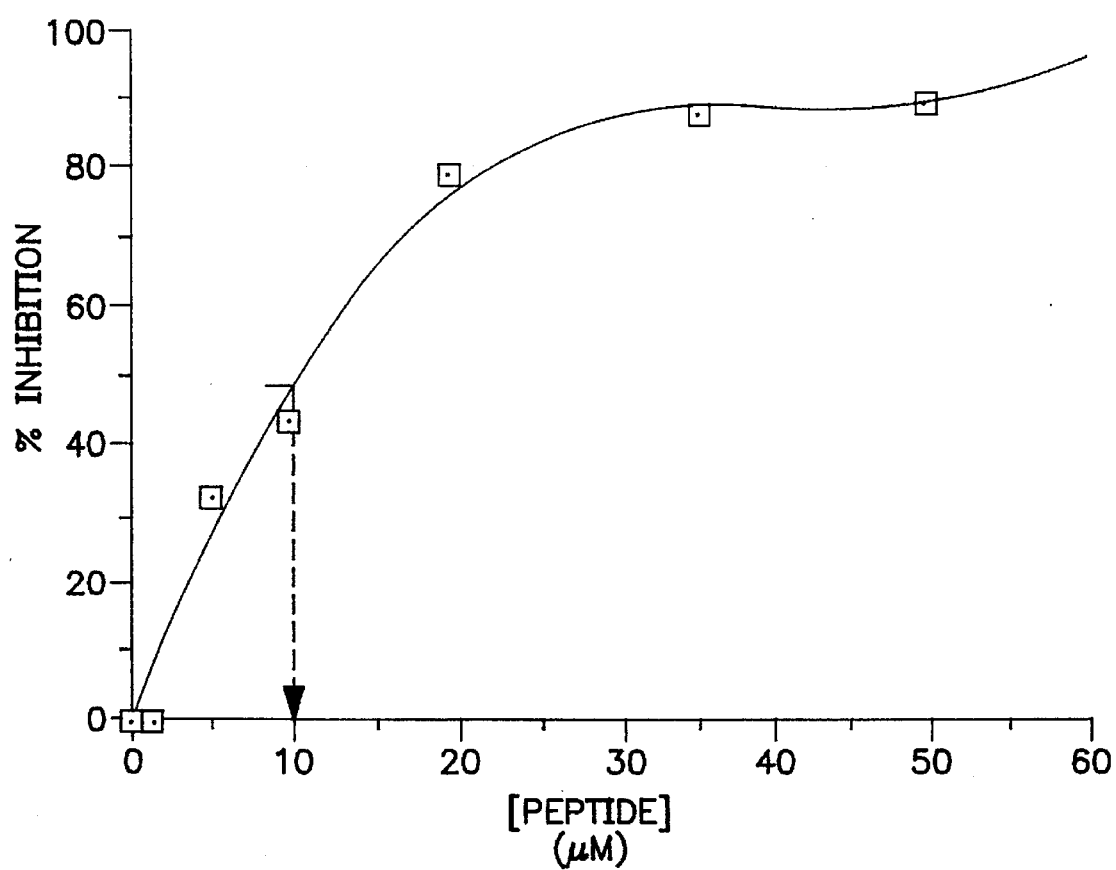
FIG. 2 depicts a plot of the percent inhibition of $p34^{cdc2}$ histone H1 kinase activity versus the p107 9mer peptide concentration.

The practice of the present invention will employ, unless otherwise indicated, conventional techniques of protein chemistry and biochemistry, molecular biology, microbiology and recombinant DNA technology, which are within the skill of the art. Such techniques are explained fully in the literature. See, e.g., Sambrook, Fritsch & Maniatis, *Molecular Cloning: A Laboratory Manual*, Second Edition (1989); *DNA Cloning*, Vols. I and II (D. N. Glover ed. 1985); *Oligonucleotide Synthesis* (M. J. Gait ed. 1984); *Nucleic Acid Hybridization* (B. D. Hames & S. J. Higgins eds. 1984); *Animal Cell Culture* (R. K. Freshney ed. 1986); *Immobilized Cells and Enzymes* (IRL press, 1986); Perbal, B., *A Practical Guide to Molecular Cloning* (1984); the series, *Methods In Enzymology* (S. Colowick and N. Kaplan eds., Academic Press, Inc.).

All patents, patent applications and publications cited herein, whether supra or infra, are hereby incorporated by reference in their entirety.

As used in this specification and the appended claims, the singular forms "a," "an" and "the" include plural references unless the content clearly dictates otherwise.

A. Definitions

In describing the present invention, the following terms will be employed, and are intended to be defined as indicated below.

By "$p34^{cdc2}$," "$p34^{cdc2}$ kinase" or "$p34^{cdc2}$ cell cycle regulatory kinase", which terms are used interchangeably, is meant an approximately 32–34 kda protein, alternatively known as MPF (maturation/M Phase promoting factor or mitosis-promoting factor), which possesses protein-serine/ threonine kinase activity (as described in Lee et al. (1987), supra; Dunphy et al. (1988), supra; and Gautier et al. (1988), supra). The term encompasses the product of the cdc2 gene of *Schizosaccharomyces pombe* and the product of the CDC28 gene from *Saccharomyces cerevisiae*, and homologues found in other species (see, Arion et al. (1988) *Cell* 55:371–378; Dunphy et al. (1988), supra; Gautier et al. (1988), supra; and Labbé et al. (1988) *Cell* 57:253–263), including the human homolog of these proteins, $p34^{cdc2}$ (Lee et al. (1987), supra). $p34^{cdc2}$ kinase activity is dependent on association with specific cyclins and post-translational modification of Thr-14 and Tyr-15 amino acid residues.

The term "$p33^{cdk2}$," "$p33^{cdk2}$ kinase" or "$p33^{cdk2}$ cell cycle regulatory kinase" refers to a cyclin-dependent kinase homolog of $p34^{cdc2}$ kinase, the activity of which is similarly dependent on association with one or more cyclin molecules (Tsai et al. (1991), supra; Rosenblatt et al. (1992) *Proc. Natl. Acad. Sci. USA* 89:2824–2828; Elledge et al. *Proc. Natl. Acad. Sci. USA* 89:2907–2911).

By "a $p34^{cdc2}$ binding domain" is meant that portion of the molecule in question (i.e., an Rb, p107 or a cyclin) which interacts either directly or indirectly with $p34^{cdc2}$ kinase thereby preventing the activation of the kinase. The binding domain may be a sequential portion of the molecule, i.e., a contiguous sequence of amino acids, or it may be conformational, i.e., a combination of non-contiguous sequences of amino acids which, when the molecule is in its native state, forms a structure which interacts with $p34^{cdc2}$ kinase.

By being "derived from" a binding domain is meant any molecular entity which is identical, substantially homologous, complementary or otherwise functionally or structurally equivalent to the native $p34^{cdc2}$ binding domain of the molecule in question (i.e., an Rb, p107 or a cyclin). Thus, a molecule derived from a particular binding domain may encompass the amino acid sequence of a naturally occurring ligand-binding site, any portion of that binding site, or other molecular entity that functions to bind to an associated ligand. A molecule derived from such a binding domain will interact either directly or indirectly with p34$^{cdc2}$ kinase in such a way as to mimic the native binding domain. Such molecular entities may include competitive inhibitors, peptide mimetics and the like.

An "inhibitor of p34$^{cdc2}$ kinase activity" or an "inhibitor of p33$^{cdk2}$ kinase activity" is intended to mean a peptide or peptide fragment derived from a p34$^{cdc2}$ binding domain of an Rb, p107 or a cyclin, which interacts either directly or indirectly with p34$^{cdc2}$ or p33$^{cdk2}$ and prevents activation of the kinase. If the inhibitor is a cyclin protein, it will not include the full-length sequence of the wild-type molecule. An inhibitor can prevent cyclin-dependent kinase activation by competitively inhibiting the binding of cyclins to p34$^{cdc2}$. In addition, peptide mimetics, synthetic molecules with physical structures designed to mimic structural features a particular peptide, may similarly serve as inhibitors of kinase activity. Such inhibitors diminish the p34$^{cdc2}$ or p33$^{cdk2}$ enzymatic catalysis of the transfer of the terminal phosphate of ATP, or a similar ATP analog or other nucleotide triphosphate, to a suitable substrate. Such substrates include histone H1, DNA polymerase α, RNA polymerase II, Rb, p53, nucleolin, cAb1, SV40 large T antigen, lamin A and the like. Alternatively, such inhibitors may diminish the ability of activated (e.g., dephosporylated) p34$^{cdc2}$ to support progression through the cell cycle as measured by a suitable cell cycle assay (see, e.g., Pines et al. (1989), supra). Such inhibition may be by a direct, competitive mechanism, or by an indirect, non- or uncompetitive mechanism.

An "inhibitor of human papillomavirus E7 protein" is a molecule which interacts with transforming protein E7, either directly or indirectly, to prevent the formation of the specific complex with Rb. As with inhibitors of p34$^{cdc2}$ kinase, these inhibitors can prevent binding by competitive inhibition, or by an indirect, non- or uncompetitive mechanism. In addition, the term encompasses peptide inhibitors as well as peptide mimetics.

The inhibitory activity of a candidate peptide or peptide mimetic can be tested by assessing the ability of the candidate to bind to the target acceptor, i.e., p34$^{cdc2}$, p33$^{cdk2}$ or HPV E7. For example, those candidates which bind to the target acceptor with suitable affinity and specificity can be assayed for their ability to inhibit the activity of the target acceptor. For p34$^{cdc2}$ and p33$^{cdk2}$, the ability of the inhibitor to diminish kinase activity can be assessed. For HPV E7, the ability of a candidate inhibitor to compete with Rb for binding to E7 can be determined. Finally, to assess the inhibitory activity in a whole cell setting, the ability of a candidate inhibitor to prevent the progression of a synchronized population of transformed cells through the cell cycle can be determined. For example, HeLa cells can be synchronized using techniques well-known in the art (see, Lew et al. (1991), supra). The inhibition of cell cycle progression through the G$_1$/S boundary is assessed by a diminution of DNA synthesis in the cell population. Inhibition of cell cycle progression through the G$_2$/M boundary is determined by the absence of mitotic activity (i.e., cell division).

"Peptide mimetics" are structures which serve as substitutes for peptides in interactions with acceptor molecules (see Morgan et al. (1989) Ann. Reports Med. Chem. 24:243–252 for a review of peptide mimetics). Peptide mimetics, as used herein, include synthetic structures which may or may not contain amino acids and/or peptide bonds, but retain the structural and functional features of a peptide ligand. The term, "peptide mimetics" also includes peptoids and oligopeptoids, which are peptides or oligomers of N-substituted amino acids (Simon et al. (1972) Proc. Natl. Acad. Sci. USA 89:9367–9371). Further included as peptide mimetics are peptide libraries, which are collections of peptides designed to be of a given amino acid length and representing all conceivable sequences of amino acids corresponding thereto. Methods for the production of peptide mimetics are described more fully below.

Two polypeptide sequences are "substantially homologous" when at least about 85% (preferably at least about 85% to 90%, and most preferably at least about 95%) of the nucleotides or amino acids match over a defined length of the molecule. As used herein, substantially homologous also refers to sequences showing identity to the specified polypeptide sequence.

The terms "polypeptide", "peptide" and "protein" are used interchangeably and refer to any polymer of amino acids (dipeptide or greater) linked through peptide bonds. Thus, the terms "polypeptide", "peptide" and "protein" include oligopeptides, protein fragments, analogues, muteins, fusion proteins and the like.

The following single-letter amino acid abbreviations are used throughout the text:

| Alanine | A | Arginine | R |
|---|---|---|---|
| Asparagine | N | Aspartic acid | D |
| Cysteine | C | Glutamine | Q |
| Glutamic acid | E | Glycine | G |
| Histidine | H | Isoleucine | I |
| Leucine | L | Lysine | K |
| Methionine | M | Phenylalanine | F |
| Proline | P | Serine | S |
| Threonine | T | Tryptophan | W |
| Tyrosine | Y | Valine | V |

B. General Methods

Figure 1:
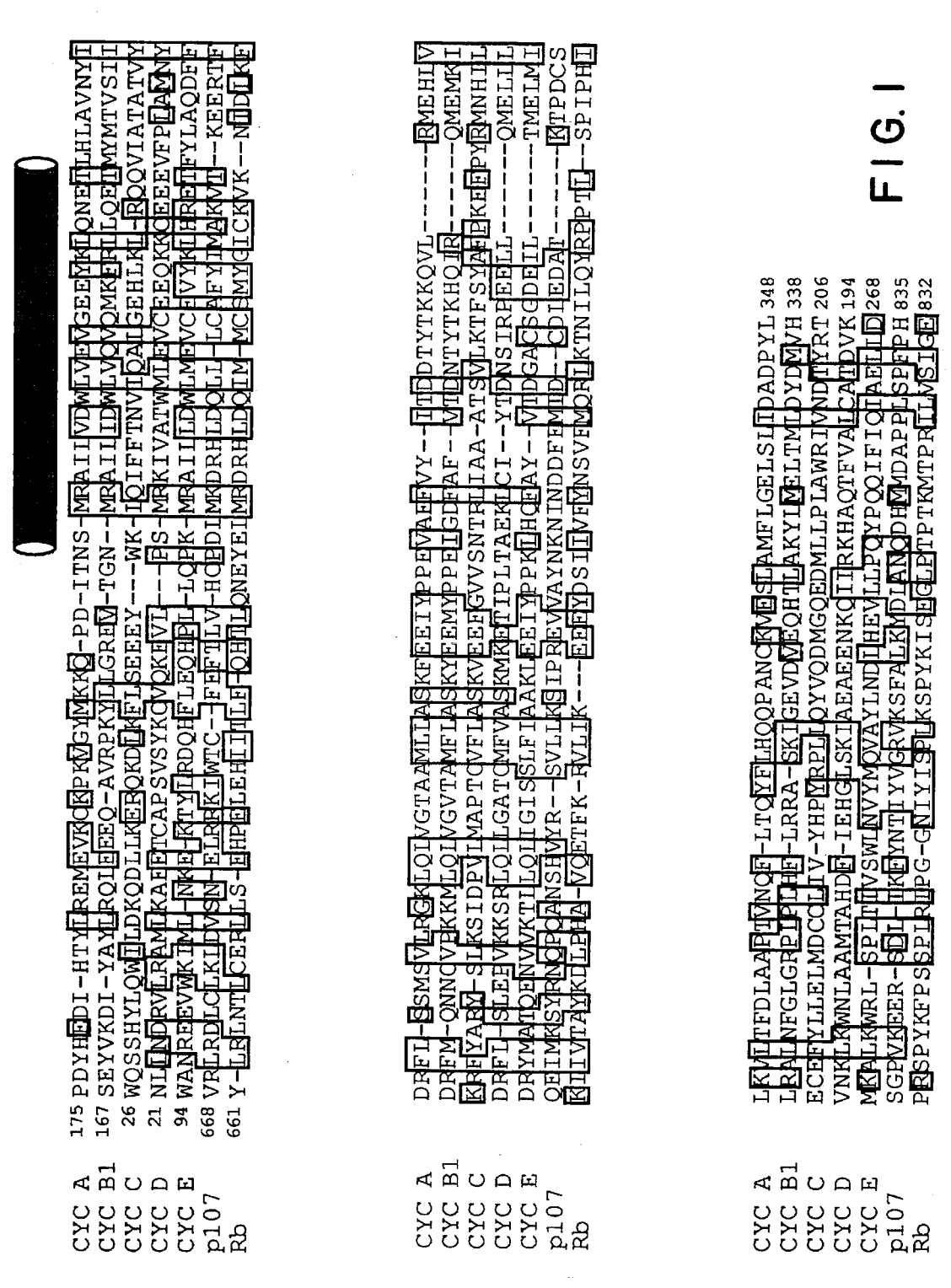

Central to the present invention is the discovery of peptide molecules which bind to and inhibit p34$^{cdc2}$ kinase activity. These molecules are derived from the binding domain of an Rb, p107 or a cyclin. These proteins, depicted in FIG. 1, bind p34$^{cdc2}$, its homolog p33$^{cdk2}$, the E2F transcription factor and the adenovirus E1A transforming protein. In addition, Rb forms a specific complex with the transforming protein of papillomavirus E7. The peptide inhibitors, and peptide mimetics thereof, provide useful tools for the analysis of the normal function of p34$^{cdc2}$ and p33$^{cdk2}$ kinases and transforming factors, such as E7, in cell growth and proliferation in precancerous and cancerous cells. Additionally, since the activity of p34$^{cdc2}$ kinase is essential for the progression through the G$_1$/S and G$_2$/M transition phases of the cell cycle, the protein inhibitors, or mimetics thereof, can be administered to cancerous tissues in order to suppress tumor growth.

As shown in the examples, the claimed inhibitors of p34$^{cdc2}$ kinase, p33$^{cdk2}$ kinase or HPV E7 include sequences of amino acids derived from the binding domains of proteins which interact with p34$^{cdc2}$ and/or HPV E7, and mimetics thereof. In particular, the inhibitors are derived from a region of homology found in a number of p34$^{cdc2}$ binding proteins known as the α-helix II region, shown in FIG. 1. A 30 amino acid peptide, FEFTLVHCPDLMKDRHLDQLLLCAFYIMAK, [SEQ ID NO: 11] encompassing the α-helix II sequence from p107 has been shown herein to bind to p34$^{cdc2}$ and p33$^{cdk2}$. This 30 amino acid peptide also inhibits the histone H1 kinase activity of p34$^{cdc2}$ and p33$^{cdk2}$. By sequentially deleting amino- or carboxy-terminal amino acids, a five amino acid sequence (CAFYI [SEQ ID NO: 3]) was identified as a minimum sequence which retains inhibitory activity. Furthermore, a peptide having nine amino acids (LCAFYIMAK [SEQ ID NO: 2]), including the 5 amino acid peptide, was shown to bind to p34$^{cdc2}$ with an affinity of approximately 10 μM. Thus, useful p34$^{cdc2}$ inhibitors of the present invention will be derived from at least this 5mer, and can include as many as 50 to 200 or more amino acids, so long as a proper binding conformation is retained.

The above-described 30mer peptide also binds to human papillomavirus (HPV) 18-E7 protein. Furthermore, the 30mer peptide inhibits E7 binding to Rb, as does a nine amino acid peptide derived from Rb (MCSMYGICK [SEQ ID NO: 2]).

As explained above, all of these peptides, as well as molecules substantially homologous, complementary or otherwise functionally or structurally equivalent to these peptides, may be used for purposes of the present invention.

The peptide inhibitors of the present invention may be synthesized by conventional techniques known in the art, for example, by chemical synthesis such as solid phase peptide synthesis. Such methods are known to those skilled in the art. In general, these methods employ either solid or solution phase synthesis methods, well known in the art. See, e.g., J. M. Stewart and J. D. Young, *Solid Phase Peptide Synthesis,* 2nd Ed., Pierce Chemical Co., Rockford, Ill. (1984) and G. Barany and R. B. Merrifield, *The Peptides: Analysis, Synthesis, Biology,* editors E. Gross and J. Meienhofer, Vol. 2, Academic Press, New York, (1980), pp. 3–254, for solid phase peptide synthesis techniques; and M. Bodansky, *Principles of Peptide Synthesis,* Springer-Verlag, Berlin (1984) and E. Gross and J. Meienhofer, Eds., *The Peptides: Analysis, Synthesis, Biology,* supra, Vol. 1, for classical solution synthesis.

As explained above, peptide mimetics which structurally and functionally mimic the peptide inhibitors described above will also find use herein and may be generated using the following strategies and procedures. Generally, mimetics are designed based on information obtained by systematic replacement of L-amino acids by D-amino acids, replacement of side chain moieties by a methyl group or pseudoisosteric groups with different electronic properties (see Hruby et al. (1990) *Biochem. J.* 268:249–262), and by systematic replacement of peptide bonds in the above described peptide inhibitors with amide bond replacements. For example, analogues containing amide bond surrogates may be used to investigate aspects of peptide structure and function, such as rotational freedom in the backbone, intra- and intermolecular hydrogen-bond patterns, modifications of local and total polarity and hydrophobicity, and oral bioavailability.

Local conformational constraints can also be introduced to determine conformational requirements for activity of a candidate peptide mimetic inhibitor of p34$^{cdc2}$, p33$^{cdk2}$, HPV E7 or other acceptor. For example, β,β-disubstituted amino acids may be used to examine the effects of conformational constraints on peptide activity (see, e.g., Manning et al. (1982) *J. Med. Chem.* 25:408–414; Mosberg et al. (1983) *Proc. Natl. Acad. Sci. USA* 106:506–512; Pelton et al. (1985) *Proc. Natl. Acad. Sci. USA* 82:236–239).

The mimetics can include isosteric amide bonds such as ψ[CH$_2$S], ψ[CH$_2$NH], ψ[CSNH$_2$], ψ[NHCO], ψ[COCH$_2$] and ψ[(E) or (Z) CH=CH] (see, for review, Spatola (1983) in "Chemistry and Biochemistry of Amino Acids, Peptides and Proteins," Volume VII, (Weinstein, ed.), Marcel Dekker, New York, 267–357). Structures which mimic the tetrahedral transition state associated with hydrolysis of a substrate bond can also be present and include hydroxymethylene, fluoroketone moieties and phosphoramidate transition state mimics (Bühlmayer et al. (1988) *J. Med. Chem.* 31:1839; Sham et al. (1988) *FEBS Lett.* 220:299; Matthews (1988) *Acc. Chem. Res* 21:333). The synthetic molecules can also include D-amino acids to stabilize or promote reverse turn conformations and to help stabilize the molecule from enzymatic degradation (see, e.g., Freidinger et al. (1985) in "Peptides: Structure and Function," (Deber et al., eds.), Pierce Chem. Co., Rockford, Ill., 549–552; Sawyer et al. (1980) *Proc. Natl. Acad. Sci. USA* 77:5754–5758; Torchiana et al. (1978) *Arch. Int. Pharmacol. Ther.* 235:170–176). Cyclic amino acid analogues may be used to constrain amino acid residues to particular conformational states, e.g., αα'- and ββ'-substituted cyclic amino acids such as 1-aminocyclopentanecarboxylic acid (cycloleucine) and β,β-cyclopentamethylene-β-mercaptopropionic acid (see Hruby et al. (1990), supra).

The mimetics can also include mimics of inhibitor peptide secondary structure—structures which can model the 3-dimensional orientation of amino acid residues into the known secondary conformations of proteins—including β-turn mimetics, such as phenoxathin ring system, and β-sheet mimics, such as epindolidione structures. Design, synthesis and conformational analysis of an α-helix inducing template has been described (Kemp et al. (1988) *Tetrahedron Lett.* 29:4931; Kemp et al. (1988) *Tetrahedron Lett.* 29:4935).

Similarly, peptoids will find use herein. Peptoids are oligomers of N-substituted amino acids (Simon et al. (1972), supra), and can be used as motifs for the generation of chemically diverse libraries of novel molecules, which can then be tested for binding and inhibitory activity against p34$^{cdc2}$, p34$^{cdk2}$, HPV E7 or other acceptor molecules. The monomers may incorporate t-butyl-based side-chain and 9-fluorenylmethoxy-carbonyl α-amine protection. Oligomerization of the peptoid monomers may be performed by, for example, in situ activation by either benzotriazol-1-yloxytris(pyrrolidino)phosphonium hexafluorphosphate or bromotris(pyrrolidino)phosphonium hexafluorophosphate. Other steps are identical to conventional peptide synthesis using α-(9-fluorenylmethoxycarbonyl)amino acids. Oligopeptoids may be identified which have affinities comparable to the corresponding inhibitory peptides and, thus, are useful in p34$^{cdc2}$ and p33$^{cdk2}$ kinase or HPV E7 binding assays (see Simon et al. (1992), supra).

Peptide ligands that interact with p34$^{cdc2}$, p33$^{cdk2}$, HPV E7 or other protein acceptors can be developed by using a biological expression system (see Christian et al. (1992) *J. Mol. Biol.* 227:711–8; Devlin et al. (1990) *Science* 249:404–406; Cwirla et al. (1990) *Proc. Natl. Acad. Sci. USA* 87:6378–6382). The use of such systems allows the production of large libraries of random peptide sequences and the screening of these libraries for peptide sequences that bind to particular proteins. The libraries may be produced by cloning synthetic DNA that encodes random peptide sequences into *Escherichia coli* expression vectors. In the filamentous phage system, foreign peptide sequences can be expressed on the surface of the infectious phage (see Smith (1985) *Science* 228:1315–1317; Parmley et al. (1988) *Gene* 73:305–318).

For example, a library may be made by ligating into an appropriate phage, a synthetic DNA fragment containing a degenerate coding sequence (NNK)$_n$, where N stands for an equal mixture of the deoxynucleotides G, A, T, and C, K stands for an equimolar mixture of G and T, and n stands for the number of amino acid residues desired in the product peptide. Affinity purification of phage displaying affector-binding peptides may be done by biotinylating the affector, incubating the phage with the biotinylated affector and reacting the phage on streptavidin-coated plates. Bound phage are eluted and amplified on agar medium and subjected to further rounds of affinity purification. Phage from later rounds of affinity purification are cloned and propagated, their DNAs sequenced to determine the amino acid sequences of their expressed peptide and their binding to p34$^{cdc2}$, p33$^{cdk2}$, HPV E7 or other affector molecules assessed by enzyme-linked immunosorbent assays (ELISA). Such libraries consisting of large numbers of clones expressing different short peptide sequences can be used to map binding domains.

Large libraries of peptide inhibitors can also be constructed by concurrent synthesis of overlapping peptides as described in U.S. Pat. No. 4,708,871 to Geysen. The synthetic peptides can be tested for interaction with acceptor molecules by ELISA while still attached to the support used for synthesis. The solid support is generally a polyethylene or polypropylene rod onto which is graft polymerized a vinyl monomer containing at least one functional group to produce polymeric chains on the carrier. The functional groups are reacted to provide primary or secondary amine groups which are sequentially reacted with amino acid residues in the appropriate order to build the desired synthetic peptide using conventional methods of solid phase peptide chemistry.

Once produced, the inhibitory peptides or peptide mimetics can be used in pharmaceutical compositions to ameliorate tumors associated with disruption of genes which code for essential cyclins, for example, hepatocellular carcinomas, parathyroid tumors, some B cell leukemias and certain breast carcinomas or tumors associated with the loss of p53 function. The inhibitory peptides of the present invention can be formulated into therapeutic compositions in a variety of dosage forms such as, but not limited to, liquid solutions or suspensions, tablets, pills, powders, suppositories, polymeric microcapsules or microvesicles, liposomes, and injectable or infusible solutions. The preferred form depends upon the mode of administration and the particular cancer type targeted. The compositions also preferably include pharmaceutically acceptable vehicles, carriers or adjuvants, well known in the art, such as human serum albumin, ion exchangers, alumina, lecithin, buffer substances such as phosphates, glycine, sorbic acid, potassium sorbate, and salts or electrolytes such as protamine sulfate. Suitable vehicles are, for example, water, saline, dextrose, glycerol, ethanol, or the like, and combinations thereof. Actual methods of preparing such compositions are known, or will be apparent, to those skilled in the art. See, e.g., *Remington's Pharmaceutical Sciences*, Mack Publishing Company, Easton, Pa., 18th edition, 1990.

The above compositions can be administered using conventional modes of delivery including, but not limited to, intravenous, intraperitoneal, oral, intralymphatic, or subcutaneous administration. Local administration, to the tumor in question, will also find use with the present invention.

Therapeutically effective doses will be easily determined by one of skill in the art and will depend on the severity and course of the disease, the patient's health and response to treatment, and the judgment of the treating physician.

C. Experimental

Below are examples of specific embodiments for carrying out the present invention. The examples are offered for illustrative purposes only, and are not intended to limit the scope of the present invention in any way.

Efforts have been made to ensure accuracy with respect to numbers used (e.g., amounts, temperatures, etc.), but some experimental error and deviation should, of course, be allowed for.

EXPERIMENTAL METHODS

HeLa Cell Lysates: HeLa cell extracts served as a source of p34$^{cdc2}$ and p33$^{cdk2}$ and were prepared as follows. HeLa cells were lysed in 20 mM N-[2-hydroxyethyl]piperazine-N'-[2-hydroxypropanesulfonic acid] (HEPES), pH 7.0, 150 mM NaCl, 5 mM sodium vanadate, 10 mM Na$_4$P$_2$O$_7$, 1 mM ZnCl$_2$, 2 mM ethylene-diaminetetraacetic acid (EDTA), 2 mM ethylene glycol-bis(β-aminoethyl ether)-N,N,N',N'-tetraacetic acid (EGTA), 1 mM dithiothreitol (DTT), 0.25% (v:v) NP-40, 1 mM Benzamidine, 1 mM phenylmethylsulfonyl fluoride (PMSF) and 20 µg/ml each: N$_2$S$_2$O$_3$, leupeptin, Antipan and Pepstatin, followed by centrifugation to remove cell debris.

Immunoprecipitation of p34$^{cdc2}$: Immunoprecipitation of p34$^{cdc2}$ from HeLa cell extracts was performed using previously reported procedures (Harlow et al. (1988) in: *Antibodies: A Laboratory Manual*, ed. Harlow and Lane, Cold Spring Harbor: Cold Spring Harbor Laboratory, pp 421–470) and anti-p34$^{cdc2}$ antibody, G6 (Gibco, BRL). Immunoprecipitation by this method yields an activated kinase complex (Draetta et al. (1988), *Cell* 54:17–26).

Assay of p34$^{cdc2}$ Kinase Activity: Histone H1 kinase reactions were performed in 50 mM Tris, pH 8.0, 10 mM MgCl$_2$, 0.5 mM DTT, 1 mM EGTA plus 0.1 mM ATP, 1 µCi γ-[$^{32}$P]-ATP and 10 µg histone H1 (Boeringer Mannheim), and a source of p34$^{cdc2}$. Reactions were incubated at 30° C. for 20 minutes and stopped by the addition of protein gel sample buffer. Kinase reactions were separated by SDS-PAGE (12.5% gel). The bands were detected by autoradiography and the amount of $^{32}$P incorporated was quantitated using an Ambis Radioanalytic Imaging System.

EXAMPLE 1

Comparison of p34$^{cdc2}$ Binding Proteins

Inhibitors of p34$^{cdc2}$ cell cycle regulatory kinase activity were identified by first comparing the primary amino acid sequence of known p34$^{cdc2}$-associated proteins: human cyclins A, B1, C, D, E, p107 protein and retinoblastoma tumor suppressor protein (Rb) [SEQ ID NOS: 4–10]. The basic alignment of the human cyclin proteins was demonstrated by Lew et al. (1991), supra, and the alignment of Rb and p107 was performed by Ewen et al. (1991), supra. The sequences of all seven proteins was subsequently compared, as depicted in FIG. 1. Secondary structure analysis of all seven sequences was performed using both Chou-Fasman (Chou et al. (1974) *Biochemistry* 13:211–222; Chou et al. (1974) *Biochemistry* 13:222–245) and Robson-Garnier (Garnier et al. (1978) *J. Mol. Biol.* 120:97–120) structure prediction programs. Two regions of common α-helical structure, designated α-helix I and α-helix II, were predicted for six of seven proteins by both structure prediction programs.

A 170 amino acid region of sequence similarity was observed among Rb, p107 and the human cyclins. Rb and p107 share the highest degree of similarity with cyclin E, 27% and 34%, respectively. These sequences contain two regions of common predicted α-helical structure. Projection of the α-helix II sequences of Rb, p107 and cyclin E on a helical wheel demonstrates that the conserved residues are displayed on one face of the α-helix.

EXAMPLE 2

Binding of p34$^{cdc2}$ to p107

In order to test whether the α-helix II domain is involved in the interaction of Rb, p107 and cyclin E with p34$^{cdc2}$, a 30 amino acid peptide from p107 (residues 692–721: FEFTLVHCPDLMKDRHLDQLLLCAFYIMAK [SEQ ID NO:11]) encompassing α-helix II, was synthesized and assayed for its ability to associate with p34$^{cdc2}$. The 30mer was covalently linked to CH-activated sepharose 4B (Pharmacia) as follows. The p107 30 amino acid peptide, which was insoluble in aqueous solutions, was linked to the sepharose in N,N-dimethylformamide. The concentration of 30mer linked to the bead was 0.85 μmole/ml as determined by HPLC. The p107 30mer-sepharose was incubated with total HeLa cell lysate and washed with 25 volumes of lysis buffer. The bound proteins were eluted with increasing concentrations of NaCl, separated by sodium dodecyl sulfate-polyacrylamide gel electrophoresis (SDS-PAGE) (12.5% gel) and transferred to polyvinylidene difluoride (PVDF) membranes. p34$^{cdc2}$ was detected by probing the membrane with anti-p34$^{cdc2}$ antibody, G6 (Gibco, BRL) (see, Draetta et al. (1988), supra).

The p107 30mer-sepharose binds to p34$^{cdc2}$ and the majority of the complex was stable to 2M NaCl. These results indicate that the amino acid sequence within α-helix II contains sufficient information to direct interaction with p34$^{cdc2}$.

EXAMPLE 3

Binding of p33$^{cdk2}$ to p107

The ability of p107 to bind to p33$^{cdk2}$ was examined using the methods described in Example 2. p107 30mer-sepharose beads were incubated with HeLa cell extract (3×10$^5$ cells per reaction) and then washed extensively. Bound complexes were then separated on a 12.5% SDS-PAGE gel and blotted onto a PVDF membrane. The blot was then probed with the kinase antibody. The results of this western blot analysis with anti-p33$^{cdk2}$ antibody (Upstate Biotechnology) indicates that the p107 30 amino acid peptide binds this kinase subunit.

EXAMPLE 4

Histone H1 Kinase Activity of Bound and Immunoprecipitated p34$^{cdc2}$

In order to examine the effect of binding of p34$^{cdc2}$ to p107 30mer-sepharose on p34$^{cdc2}$ kinase activity, histone H1 kinase activities associated with p107 30mer-sepharose and immunoprecipitated p34$^{cdc2}$ were compared as follows. p34$^{cdc2}$ was bound to p107 30mer-sepharose as described in Example 2. Histone H1 kinase reactions were performed using either immunoprecipitated or p107 30mer-sepharose bound p34$^{cdc2}$. The amount of p34$^{cdc2}$ bound to p107 30mer-sepharose was compared with that contained within the immune complex by western blot. Two times the amount of immunoprecipitated p34$^{cdc2}$ used in the kinase reaction was blotted to facilitate easier detection. The amount of p34$^{cdc2}$ associated with the p107 30mer-sepharose was determined by densitometry to be ≧50 time greater than contained within the immune complexes. This data was used in normalizing the kinase activity associated with the different beads.

The observed histone H1 kinase activity for the p107 30 amino acid peptide-bound enzyme is similar to that of the immune complex. Normalization for the amount of p34$^{cdc2}$ protein present in both reactions demonstrated that the peptide bound enzyme has a specific activity equal to only 1.4% the specific activity of the immune complex. This is consistent with p107 30mer competing for cyclin binding to p34$^{cdc2}$, and is indicative of a common mechanism of binding for the cyclins, Rb, and p107.

EXAMPLE 5

Peptide Inhibition of p34$^{cdc2}$ Histone H1 Kinase Activity

As a further test of the association of p107 with p34$^{cdc2}$, and to define the minimal sequence necessary for interaction with p34$^{cdc2}$, the effect of p107 peptides on the p34$^{cdc2}$ immune complex histone H1 kinase activity was assessed. Both amino- and carboxy-terminal deletions were introduced into the original 30 amino acid peptide (see Table 1). The peptides were synthesized by standard methods and purified by HPLC. Immune complexes were formed as described in Example 4 and resuspended in kinase buffer plus 50 μM of the respective peptide solubilized in N,N-dimethylformamide, or an equal volume of solvent. After incubating the reactions for 15 minutes on ice, histone H1 and γ-[$^{32}$P]-ATP were added and the kinase assays were performed and quantitated as described in Example 4.

Addition of the p107 peptides inhibits histone H1 kinase activity associated with the immune complex (see Table 1). Addition of the p107 peptides to a p33$^{cdk2}$ kinase reaction also inhibits the activity of the kinase.

Peptides with deletions of the amino-terminal sequences to Cys$_{713}$ and carboxy-terminal sequences to Ile$_{717}$ retain the ability to inhibit p34$^{cdc2}$ activity. Further deletions to either Ala$_{714}$ or Tyr$_{716}$ resulted in inactive peptides. An unrelated 19mer control peptide had no effect upon histone H1 activity.

These data demonstrate that the minimal sequence which retained inhibitory activity was a pentapeptide with the sequence CAFYI [SEQ ID NO: 3]. Non-conservative amino acid substitutions within the pentapeptide totally abrogated p34$^{cdc2}$ kinase inhibition except at Cys$_{713}$.

EXAMPLE 6

Effect of Single Amino Acid Substitution on p34$^{cdc2}$ Inhibitory Activity of p107 Peptides In order to examine the role for Cys$_{706}$ of Rb and Cys$_{713}$ of p107 in the binding of p34$^{cdc2}$ and other ligands such as E1A or E2F, a peptide was synthesized which contained the Cys to Phe amino acid substitution at position 713 and its inhibitory activity was examined. This single mutation resulted in a 30% decrease in the peptide's ability to inhibit histone H1 kinase activity, confirming the importance of Cys$_{713}$ in the p107 peptide-p34$^{cdc2}$ interaction (see Table 1, 9mer versus 713CF. This residue is also conserved in cyclins D and E and may function in a similar manner. In addition, the substitution of Ala for Tyr$_{716}$, which is highly conserved between the other proteins examined, totally abrogated p34$^{cdc2}$ kinase inhibition (see Table 1, 9mer versus 716YA. These data also suggest that the p107 peptides are capable of competing for and displacing cellular factors bound to p34$^{cdc2}$, which are required for kinase activation (Pines et al. (1989), supra; Murray et al. (1989), supra; Solomon et al. (1990), supra; Draetta et al. (1989) *Cell* 56:829–838) and are consistent with the earlier observation that low levels of kinase activity are associated with the p107 30mer peptide-sepharose.

with anti-p34$^{cdc2}$ antibodies and can be used to quantitate the affinity of the p107 wild type and mutant peptides for the p34$^{cdc2}$ kinase in addition to the kinase inhibition assay described in Example 7. A summary of all modifications to the original p107 peptides and their effect on binding and kinase inhibition is presented in Table 1. The affinity of the

TABLE 1

|  |  | [SEQ ID NO.] | p34$^{cdc2}$ Inhib. (%) | IC$_{50}$ (μM) |
|---|---|---|---|---|
| 30mer | FEFTLVHCPDLMKDRHLDQLLLCAFYIMAK | 11 | ND | ND |
| 21mer | DLMKDRHLDQLLLCAFYIMAK | 12 | 70 | ND |
| 18mer | KDRHLDQLLLCAFYIMAK | 13 | 80 | ND |
| 14mer | LDQLLLCAFYIMAK | 14 | 80 | ND |
| 9mer | LCAFYIMAK | 1 | 90 | 9 |
| N7mer | AFYIMAK | 15 | 0 | ND |
| N5mer | YIMAK | 16 | 0 | >100 |
| C7mer | LCAFYIM | 17 | 70 | ND |
| C6mer | LCAFYI | 18 | 79 | ND |
| C5mer | LCAFY | 19 | 0 | nd |
| NC5mer | CAFYI | 3 | 82 | 13 |
| NC4mer | CAFY | 20 | 0 | ND |
| 713CF | LFAFYIMAK | 21 | 60 | 15 |
| 714AE | LCEFYIMAK | 22 | 0 | 23 |
| 715FA | LCAAYIMAK | 23 | 0 | >100 |
| 715FK | LCAKYIMAK | 24 | 0 | >100 |
| 715FY | LCAYYIMAK | 25 | 20 | 45 |
| 716YA | LCAFAIMAK | 26 | 0 | 40 |
| 716YF | LCAFFIMAK | 27 | 80 | 25 |
| 717IK | LCAFYKMAK | 28 | 0 | >100 |
| 719AQ | LCAFYIMQK | 29 | 75 | ND |
| SV-NC5mer | PKKKRKVCAFYI | 30 | 0 | ND |
| RR-NC5mer | RRCAFYI | 31 | 0 | ND |
| PKG-NC5mer | RKRCAFYI | 32 | 0 | ND |
| SPKK-NC5mer | SPKKGCAFYI | 33 | 0 | ND |
| NC5mer-SPKK | CAFYIGSPKK | 34 | 80 | ND |

EXAMPLE 7

Affinity of the p107 9mer for p34$^{cdc2}$ Assayed by Inhibition of Histone H1 Kinase Activity The binding affinity of the 9mer peptide for p34$^{cdc2}$ was approximated by relating the percent inhibition of histone H1 kinase activity to peptide concentration. Reactions were performed as described in Example 4. The percent inhibition was quantitated using an Ambis Radioanalytic Imaging System. The percent inhibition was plotted versus the peptide concentration. In calculating a binding constant, it was assumed that the concentration of substrate and peptide were in vast excess of the p34$^{cdc2}$ protein, which was assumed to be limiting in the reaction.

As depicted in FIG. 2, the k$_d$ was calculated from the point of 50% inhibition, yielding a k$_d \approx 10$ μM. The binding affinity of the peptide for p34$^{cdc2}$ may be similar to that of the whole molecule due to the ability of the peptide to efficiently inhibit p34$^{cdc2}$ activity, which is directly related to its ability to compete with activating factors.

EXAMPLE 8

Affinity of the p107 9mer for p34$^{cdc2}$ Assayed by ELISA

An ELISA based assay was developed to measure the activity of p107 peptides and their derivatives. A 96-well cluster plate coated with the p107 30mer binds to p34$^{cdc2}$ kinase from cell extracts. This binding is easily detectable p107 9mer peptide for p34$^{cdc2}$ kinase is approximately 10 μM as measured by the ELISA based competition assay, which is in agreement with the binding constant approximated from the kinase inhibition assay as described in Example 7.

Introduction of a non-conservative amino acid substitution within the pentapeptide sequence CAFYI [SEQ ID NO: 3] resulted in substantial decreases in both p34$^{cdc2}$ inhibition and kinase binding except at Cys$_{713}$.

These data demonstrate that p107 protein is capable of associating with p34$^{cdc2}$. This is consistent with its homology to Rb and the cyclin proteins, and presents a structural basis for the functional similarities shared by these proteins.

EXAMPLE 9

Inhibition of Human Papillomavirus-E7 Protein

Rb and p107 form specific complexes with the adenovirus E1A oncoprotein and Rb forms a similar complex with the E7 oncoprotein human papillomavirus (HPV). In order to determine whether the p107 30mer peptide domain and Rb may interact with other tumor suppressor proteins or other cellular and viral ligands, p107 30mer peptide binding to cellular and bacterially expressed human papillomavirus (HPV)-E7 protein was examined. p107 30 amino acid peptide-sepharose, prepared as described in Example 2, was incubated with CaSki cell (HPV-16 positive cervical carcinoma) extract and assayed for the binding of E7 protein. Western blot analysis demonstrated that the peptide did bind to HPV16-E7 protein from CaSki cells.

Figure 3A:
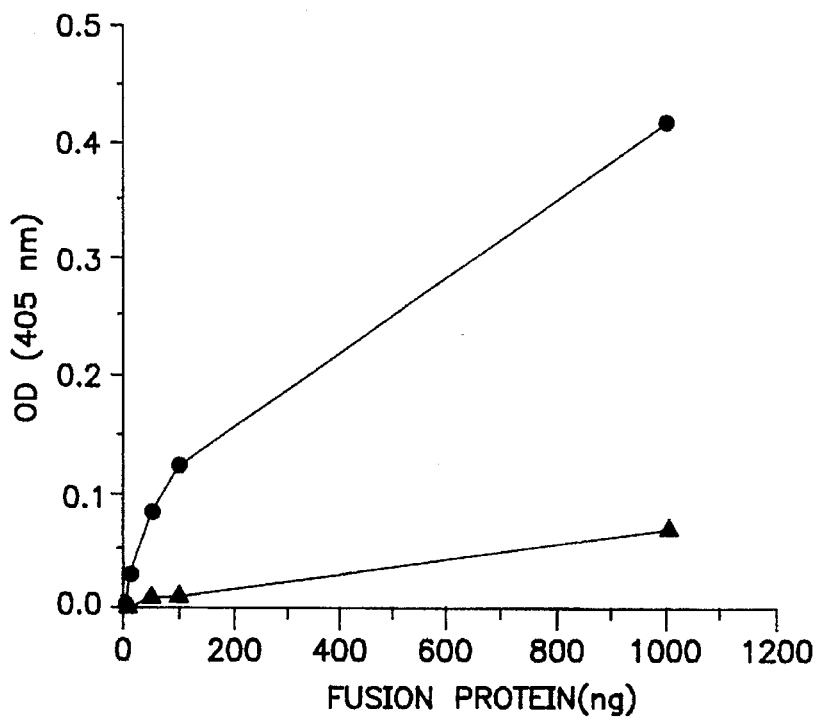
FIGS. 3A and 3B depict plots of the binding of the p107 30mer peptide to HPV18-E7 (FIG. 3A: MBP-E7 (●), MBP alone (■)) or competition for the E7-p107 30mer peptide interaction with the p107 9mer peptide (LCAFYIMAK [SEQ ID NO: 1]) (FIG. 3B).
Figure 3B:
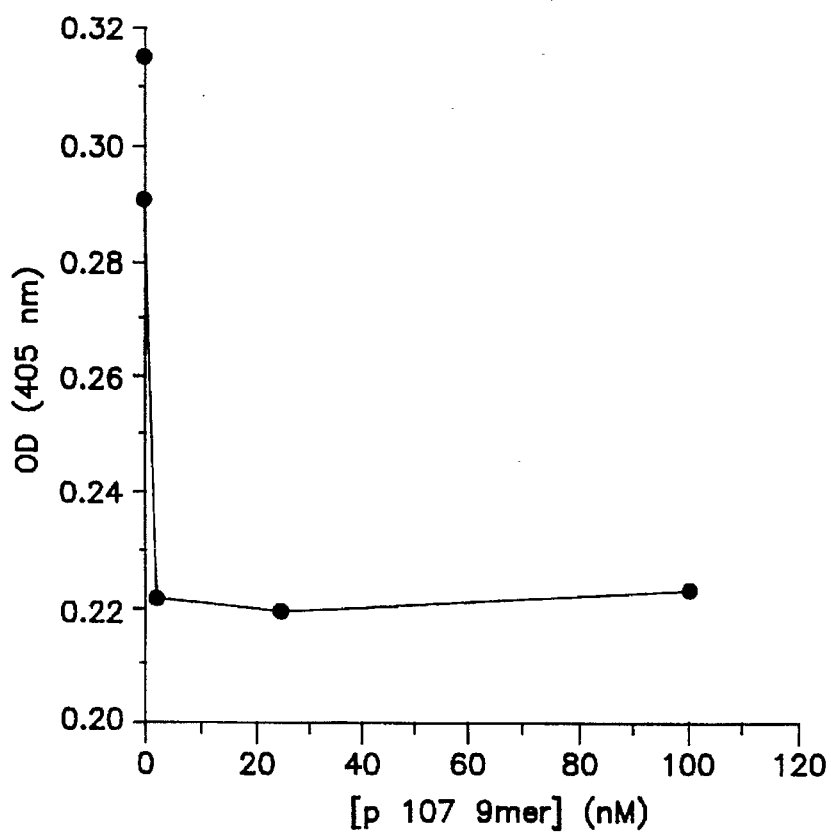

The association of bacterially expressed HPV18-E7 protein with the p107 30mer peptide was analyzed using an ELISA assay. In the experiment depicted in FIG. 3A, a 96-well cluster plate was coated with p107 30mer peptide and incubated with increasing concentration of a MBP-E7 fusion protein or the MBP protein as a control. This experiment indicates that the p107 30mer peptide can bind directly to HPV-E7 protein and that binding is not dependent upon virus type. In the experiment depicted in FIG. 3B, MBP-E7 fusion protein (100 ng) was incubated with a p107 30mer peptide-coated plate in the presence of increasing concentrations of free p107 9mer peptide. As shown in FIG. 3, binding is directly proportional to the increase in the optical density at 405 nm. The results of competition experiments shown in FIG. 3B indicate that the affinity of the p107 9mer peptide for the HPV18-E7 protein is approximately 1 nM, which is approximately 10,000-fold greater than for the $p34^{cdc2}$ kinase.

EXAMPLE 10

ELISA Assay of p107 Competition for E7-Rb Complex Formation

Figure 4A:
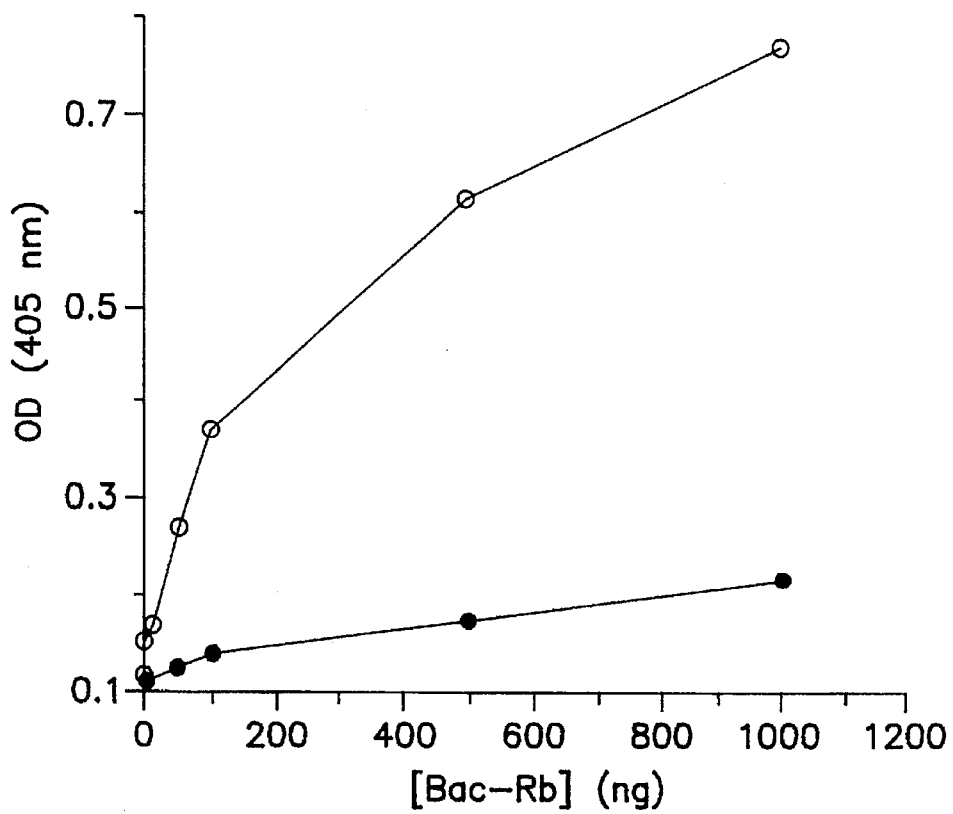
FIGS. 4A and 4B depict plots of the effect of p107 9mer peptide (LCAFYIMAK [SEQ ID NO: 1]) on the binding of MBP-E7 protein to Rb protein as determined by ELISA (FIG. 4A: MBP-E7 (O); MBP alone (●)) or by binding competition (FIG. 4B: Rb bound (●)).
Figure 4B:
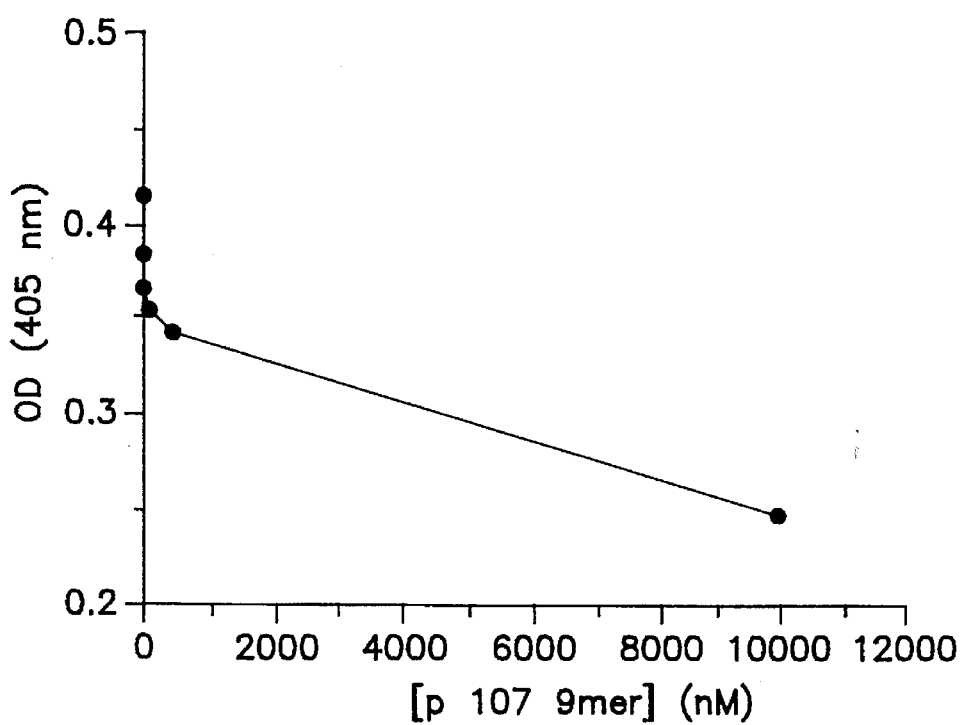

To examine the effect of p107 peptide binding upon the E7-Rb interaction, an ELISA assay was used to monitor E7-Rb complex formation. 96-well cluster plates were coated with either MBP-E7 protein (O) or MBP alone as a control (●). The plates were incubated with increasing concentrations of baculovirus expressed Rb which was detected with monoclonal antibody αRb349 (Pharmingen, San Diego Calif.) (FIG. 4A). In a separate experiment, 96-well cluster plates were coated with MBP-E7 protein and incubated with 100 ng Rb in the presence of increasing concentrations of p107 9mer peptide (FIG. 4B). Binding is quantitated as an increase in optical density at 405 nm. The results of the experiments depicted in FIG. 4A clearly demonstrate the ability of bacterially expressed E7-MBP fusion protein to bind to Rb. The results of the experiment shown in FIG. 4B demonstrate that addition of increasing concentrations of p107 9mer peptide to the reaction effectively competes for E7 association with Rb. This result suggests that the p107 9mer peptide may be an effective inhibitor of HPV-E7 protein. A corresponding peptide from Rb protein (sequence MCSMYGICK [SEQ ID NO: 2]) also binds to the E7 oncoprotein and competes for the E7-Rb interaction.

Thus, inhibitors of $p34^{cdc2}$ and $p33^{cdk2}$, as well as inhibitors of human papillomavirus, have been disclosed. Although preferred embodiments of the subject invention have been described in some detail, it is understood that obvious variations can be made without departing from the spirit and the scope of the invention as defined by the appended claims.

What is claimed:

1. An inhibitor of p34$^{cdc2}$ cell cycle regulatory kinase activity, or an inhibitor of the kinase activity of p33$^{cdk2}$, wherein the inhibitor is derived from the alpha-helix II domain of p107 and further wherein the inhibitor comprises a peptide including the amino acid sequence CAFYI (SEQ ID NO:3), or a peptide including substitutions of the sequence CAFYI (SEQ ID NO:3) which retain inhibitory activity.

2. The inhibitor according to claim 1, wherein the inhibitor comprises a peptide including the amino acid sequence CAFYI (SEQ ID NO:3).

3. The inhibitor according to claim 2, wherein the inhibitor is DLMKDRHLDQLLLCAFYIMAK (SEQ ID NO:12), KDRHLDQLLLCAFYIMAK (SEQ ID NO:13), LDQLLL-CAFYIMAK (SEQ ID NO:14), LCAFYIMAK (SEQ ID NO:1), LCAFYIM (SEQ ID NO:17), CAFYI (SEQ ID NO:3), or CAFYIGSPKK (SEQ ID NO:34).

4. The inhibitor according to claim 1, wherein the inhibitor comprises a peptide including substitutions of the sequence CAFYI (SEQ ID NO:3) which retain inhibitory activity.

5. The inhibitor according to claim 4, wherein the inhibitor is LFAFYIMAK (SEQ ID NO: 21), LCAYYIMAK (SEQ ID NO:25), LCAFFIMAK (SEQ ID NO:27), or LCAFY-IMQK (SEQ ID NO:29).

* * * * *

SEQUENCE LISTING ( 1 ) GENERAL INFORMATION:

( i i i ) NUMBER OF SEQUENCES: 34

( 2 ) INFORMATION FOR SEQ ID NO:1:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:1:

Leu Cys Ala Phe Tyr Ile Met Ala Lys
    1                       5

( 2 ) INFORMATION FOR SEQ ID NO:2:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:2:

Met Cys Ser Met Tyr Gly Ile Cys Lys
    1                       5

( 2 ) INFORMATION FOR SEQ ID NO:3:

(i) SEQUENCE CHARACTERISTICS:
    (A) LENGTH: 5 amino acids
    (B) TYPE: amino acid
    (C) STRANDEDNESS: single
    (D) TOPOLOGY: linear (ii) MOLECULE TYPE: peptide (xi) SEQUENCE DESCRIPTION: SEQ ID NO:3:

```
Cys  Ala  Phe  Tyr  Ile
1                    5
```

(2) INFORMATION FOR SEQ ID NO:4:

(i) SEQUENCE CHARACTERISTICS:
        (A) LENGTH: 173 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:4:

```
Pro  Asp  Tyr  His  Glu  Asp  Ile  His  Thr  Tyr  Leu  Arg  Glu  Met  Glu  Val
1                   5                        10                      15
Lys  Cys  Lys  Pro  Lys  Val  Gly  Tyr  Met  Lys  Lys  Gln  Pro  Asp  Ile  Thr
                    20                       25                      30
Asn  Ser  Met  Arg  Ala  Ile  Leu  Val  Asp  Trp  Leu  Val  Glu  Val  Gly  Glu
               35                      40                      45
Glu  Tyr  Lys  Leu  Gln  Asn  Glu  Thr  Leu  His  Leu  Ala  Val  Asn  Tyr  Ile
     50                       55                      60
Asp  Arg  Phe  Leu  Ser  Ser  Met  Ser  Val  Leu  Arg  Gly  Lys  Leu  Gln  Leu
65                       70                      75                          80
Val  Gly  Thr  Ala  Ala  Met  Leu  Leu  Ala  Ser  Lys  Phe  Glu  Glu  Ile  Tyr
                    85                      90                      95
Pro  Pro  Glu  Val  Ala  Glu  Phe  Val  Tyr  Ile  Thr  Asp  Asp  Thr  Tyr  Thr
                    100                     105                     110
Lys  Lys  Gln  Val  Leu  Arg  Met  Glu  His  Leu  Val  Leu  Lys  Val  Leu  Thr
               115                     120                     125
Phe  Asp  Leu  Ala  Ala  Pro  Thr  Val  Asn  Gln  Phe  Leu  Thr  Gln  Tyr  Phe
     130                     135                     140
Leu  His  Gln  Gln  Pro  Ala  Asn  Cys  Lys  Val  Glu  Ser  Leu  Ala  Met  Phe
145                     150                     155                         160
Leu  Gly  Glu  Leu  Ser  Leu  Ile  Asp  Ala  Asp  Pro  Tyr  Leu
               165                     170
```

(2) INFORMATION FOR SEQ ID NO:5:

(i) SEQUENCE CHARACTERISTICS:
        (A) LENGTH: 171 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:5:

```
Ser  Glu  Tyr  Val  Lys  Asp  Ile  Tyr  Ala  Tyr  Leu  Arg  Gln  Leu  Glu  Glu
1                   5                        10                      15
Glu  Gln  Ala  Val  Arg  Pro  Lys  Tyr  Leu  Leu  Gly  Arg  Glu  Val  Thr  Gly
                    20                       25                      30
Asn  Met  Arg  Ala  Ile  Leu  Ile  Asp  Trp  Leu  Val  Gln  Val  Gln  Met  Lys
               35                      40                      45
```

```
Phe  Arg  Leu  Leu  Gln  Glu  Thr  Met  Tyr  Met  Thr  Val  Ser  Ile  Ile  Asp
     50                 55                      60

Arg  Phe  Met  Gln  Asn  Asn  Cys  Val  Pro  Lys  Lys  Met  Leu  Gln  Leu  Val
65                      70                 75                            80

Gly  Val  Thr  Ala  Met  Phe  Leu  Ala  Ser  Lys  Tyr  Glu  Glu  Met  Tyr  Pro
                    85                      90                      95

Pro  Glu  Ile  Gly  Asp  Phe  Ala  Phe  Val  Thr  Asp  Asn  Thr  Tyr  Thr  Lys
               100                      105                      110

His  Gln  Ile  Arg  Gln  Met  Glu  Met  Lys  Ile  Leu  Arg  Ala  Leu  Asn  Phe
          115                      120                      125

Gly  Leu  Gly  Arg  Pro  Leu  Pro  Leu  His  Phe  Leu  Arg  Arg  Ala  Ser  Lys
     130                      135                      140

Ile  Gly  Glu  Val  Asp  Val  Glu  Gln  His  Thr  Leu  Ala  Lys  Tyr  Leu  Met
145                      150                      155                      160

Glu  Leu  Thr  Met  Leu  Asp  Tyr  Asp  Met  Val  His
                    165                      170
```

( 2 ) INFORMATION FOR SEQ ID NO:6:

( i ) SEQUENCE CHARACTERISTICS:
        ( A ) LENGTH: 179 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:6:

```
Trp  Gln  Ser  Ser  His  Tyr  Leu  Gln  Trp  Ile  Leu  Asp  Lys  Gln  Asp  Leu
1                   5                        10                      15

Leu  Lys  Glu  Arg  Gln  Lys  Asp  Leu  Lys  Phe  Leu  Ser  Glu  Glu  Glu  Tyr
          20                      25                      30

Trp  Lys  Leu  Gln  Ile  Phe  Phe  Thr  Asn  Val  Ile  Gln  Ala  Leu  Gly  Glu
     35                      40                      45

His  Leu  Lys  Leu  Arg  Gln  Gln  Val  Ile  Ala  Thr  Ala  Thr  Val  Tyr  Lys
     50                      55                      60

Arg  Phe  Tyr  Ala  Arg  Tyr  Ser  Leu  Lys  Ser  Ile  Asp  Pro  Val  Leu  Met
65                       70                      75                      80

Ala  Pro  Thr  Cys  Val  Phe  Leu  Ala  Ser  Lys  Val  Glu  Glu  Phe  Gly  Val
                    85                      90                      95

Val  Ser  Asn  Thr  Arg  Leu  Ile  Ala  Ala  Ala  Thr  Ser  Val  Leu  Lys  Thr
               100                      105                      110

Phe  Ser  Tyr  Ala  Phe  Pro  Lys  Glu  Phe  Pro  Tyr  Arg  Met  Asn  His  Ile
          115                      120                      125

Leu  Glu  Cys  Glu  Phe  Tyr  Leu  Leu  Glu  Leu  Met  Asp  Cys  Cys  Leu  Ile
     130                      135                      140

Val  Tyr  His  Pro  Tyr  Arg  Pro  Leu  Leu  Gln  Tyr  Val  Gln  Asp  Met  Gly
145                      150                      155                      160

Gln  Glu  Asp  Met  Leu  Leu  Pro  Leu  Ala  Trp  Arg  Ile  Val  Asn  Asp  Thr
                    165                      170                      175

Tyr  Arg  Thr
```

( 2 ) INFORMATION FOR SEQ ID NO:7:

( i ) SEQUENCE CHARACTERISTICS:
        ( A ) LENGTH: 173 amino acids
        ( B ) TYPE: amino acid
        ( C ) STRANDEDNESS: single (D) TOPOLOGY: linear (ii) MOLECULE TYPE: peptide (xi) SEQUENCE DESCRIPTION: SEQ ID NO:7:

```
Asn Leu Leu Asn Asp Arg Val Leu Arg Ala Met Leu Lys Ala Glu Glu
1               5                   10                  15

Thr Cys Ala Pro Ser Val Ser Tyr Lys Cys Val Gln Lys Glu Val Leu
            20                  25                  30

Pro Ser Met Arg Lys Ile Val Ala Thr Trp Met Leu Glu Val Cys Glu
        35                  40                  45

Glu Gln Lys Lys Cys Glu Glu Glu Val Phe Pro Leu Ala Met Asn Tyr
    50                  55                  60

Asp Arg Phe Leu Ser Leu Glu Pro Val Lys Lys Ser Arg Leu Gln Leu
65                  70                  75                  80

Leu Gly Ala Thr Cys Met Phe Val Ala Ser Lys Met Lys Glu Thr Ile
                85                  90                  95

Pro Leu Thr Ala Glu Lys Leu Cys Ile Tyr Thr Asp Asn Ser Ile Arg
            100                 105                 110

Pro Glu Glu Leu Leu Gln Met Glu Leu Leu Leu Val Asn Lys Leu Lys
        115                 120                 125

Trp Asn Leu Ala Ala Met Thr Ala His Asp Phe Ile Glu His Gly Leu
    130                 135                 140

Ser Lys Ile Ala Glu Ala Glu Glu Asn Lys Gln Ile Ile Arg Lys His
145                 150                 155                 160

Ala Gln Thr Phe Val Ala Leu Cys Ala Thr Asp Val Lys
                165                 170
```

(2) INFORMATION FOR SEQ ID NO:8:

(i) SEQUENCE CHARACTERISTICS:
    (A) LENGTH: 174 amino acids
    (B) TYPE: amino acid
    (C) STRANDEDNESS: single
    (D) TOPOLOGY: linear (ii) MOLECULE TYPE: peptide (xi) SEQUENCE DESCRIPTION: SEQ ID NO:8:

```
Trp Ala Asn Arg Glu Glu Val Trp Lys Ile Met Leu Asn Lys Glu Lys
1               5                   10                  15

Thr Tyr Leu Arg Asp Gln His Phe Leu Glu Gln His Pro Leu Leu Gln
            20                  25                  30

Pro Lys Met Arg Ala Ile Leu Leu Asp Trp Leu Met Glu Val Cys Glu
        35                  40                  45

Val Tyr Lys Leu His Arg Glu Thr Phe Tyr Leu Ala Gln Asp Phe Phe
    50                  55                  60

Asp Arg Tyr Met Ala Thr Gln Glu Asn Val Val Lys Thr Leu Leu Gln
65                  70                  75                  80

Leu Ile Gly Ile Ser Ser Leu Phe Ile Ala Ala Lys Leu Glu Glu Ile
                85                  90                  95

Tyr Pro Pro Lys Leu His Gln Phe Ala Tyr Val Thr Asp Gly Ala Cys
            100                 105                 110

Ser Gly Asp Glu Ile Leu Thr Met Glu Leu Met Ile Met Lys Ala Leu
        115                 120                 125

Lys Trp Arg Leu Ser Pro Leu Thr Ile Val Ser Trp Leu Asn Val Tyr
    130                 135                 140

Met Gln Val Ala Tyr Leu Asn Asp Leu His Glu Val Leu Leu Pro Gln
```

145                                          150                                          155                                          160

Tyr   Pro   Gln   Gln   Ile   Phe   Ile   Gln   Ile   Ala   Glu   Leu   Leu   Asp
                                                                                     165                                170

( 2 ) INFORMATION FOR SEQ ID NO:9:

( i ) SEQUENCE CHARACTERISTICS:
      ( A ) LENGTH: 168 amino acids
      ( B ) TYPE: amino acid
      ( C ) STRANDEDNESS: single
      ( D ) TOPOLOGY: linear ( i i ) MOLECULE TYPE: peptide ( x i ) SEQUENCE DESCRIPTION: SEQ ID NO:9:

Val   Arg   Leu   Arg   Asp   Leu   Cys   Leu   Lys   Leu   Asp   Val   Ser   Asn   Glu   Leu
   1                       5                             10                                  15

Arg   Arg   Lys   Ile   Trp   Thr   Cys   Phe   Glu   Phe   Thr   Leu   Val   His   Cys   Pro
                           20                            25                      30

Asp   Leu   Met   Lys   Asp   Arg   His   Leu   Asp   Gln   Leu   Leu   Leu   Cys   Ala   Phe
                     35                      40                            45

Tyr   Ile   Met   Ala   Lys   Val   Thr   Lys   Glu   Glu   Arg   Thr   Phe   Gln   Glu   Ile
         50                            55                      60

Met   Lys   Ser   Tyr   Arg   Asn   Gln   Pro   Gln   Ala   Asn   Ser   His   Val   Tyr   Arg
   65                            70                      75                                  80

Ser   Val   Leu   Leu   Lys   Ser   Ile   Pro   Arg   Glu   Val   Val   Ala   Tyr   Asn   Lys
                           85                      90                            95

Asn   Ile   Asn   Asp   Asp   Phe   Glu   Met   Ile   Asp   Cys   Asp   Leu   Glu   Asp   Ala
                     100                     105                           110

Thr   Lys   Thr   Pro   Asp   Cys   Ser   Ser   Gly   Pro   Val   Lys   Glu   Glu   Arg   Ser
               115                           120                           125

Asp   Leu   Ile   Lys   Phe   Tyr   Asn   Thr   Ile   Tyr   Val   Gly   Arg   Val   Lys   Ser
         130                           135                     140

Phe   Ala   Leu   Lys   Tyr   Asp   Leu   Ala   Asn   Gln   Asp   His   Met   Met   Asp   Ala
   145                           150                           155                           160

Pro   Pro   Leu   Ser   Pro   Phe   Pro   His
                           165

( 2 ) INFORMATION FOR SEQ ID NO:10:

( i ) SEQUENCE CHARACTERISTICS:
      ( A ) LENGTH: 173 amino acids
      ( B ) TYPE: amino acid
      ( C ) STRANDEDNESS: single
      ( D ) TOPOLOGY: linear ( i i ) MOLECULE TYPE: peptide ( x i ) SEQUENCE DESCRIPTION: SEQ ID NO:10:

Tyr   Leu   Arg   Leu   Asn   Thr   Leu   Cys   Glu   Arg   Leu   Leu   Ser   Glu   His   Pro
   1                       5                             10                                  15

Glu   Leu   Glu   His   Ile   Ile   Thr   Leu   Phe   Gln   His   Thr   Leu   Gln   Asn   Glu
                           20                            25                      30

Tyr   Glu   Leu   Met   Arg   Asp   Arg   His   Leu   Asp   Gln   Ile   Met   Met   Cys   Ser
                     35                      40                            45

Met   Tyr   Gly   Ile   Cys   Lys   Val   Lys   Asn   Ile   Asp   Leu   Lys   Phe   Lys   Ile
         50                            55                      60

Ile   Val   Thr   Ala   Tyr   Lys   Asp   Leu   Pro   His   Ala   Val   Gln   Glu   Thr   Phe
   65                            70                      75                                  80

Lys   Arg   Val   Leu   Ile   Lys   Glu   Glu   Glu   Tyr   Asp   Ser   Ile   Ile   Val   Phe

|     |     |     |     | 85  |     |     |     |     | 90  |     |     |     |     | 95  |
| --- | --- | --- | --- | --- | --- | --- | --- | --- | --- | --- | --- | --- | --- | --- |
| Tyr | Asn | Ser | Val | Phe | Met | Gln | Arg | Leu | Lys | Thr | Asn | Ile | Leu | Gln | Tyr |
|     |     |     | 100 |     |     |     |     | 105 |     |     |     | 110 |     |     |
| Arg | Pro | Pro | Thr | Leu | Ser | Pro | Ile | Pro | His | Ile | Pro | Arg | Ser | Pro | Tyr |
|     |     | 115 |     |     |     | 120 |     |     |     |     | 125 |     |     |     |
| Lys | Phe | Pro | Ser | Ser | Pro | Leu | Arg | Ile | Pro | Gly | Gly | Asn | Ile | Tyr | Ile |
|     | 130 |     |     |     |     | 135 |     |     |     | 140 |     |     |     |     |
| Ser | Pro | Leu | Lys | Ser | Pro | Tyr | Lys | Ile | Ser | Glu | Gly | Leu | Pro | Thr | Pro |
| 145 |     |     |     |     | 150 |     |     |     | 155 |     |     |     |     |     | 160 |
| Thr | Lys | Met | Thr | Pro | Arg | Ile | Leu | Val | Ser | Ile | Gly | Glu |
|     |     |     |     | 165 |     |     |     |     | 170 |     |     |     |

( 2 ) INFORMATION FOR SEQ ID NO:11:

( i ) SEQUENCE CHARACTERISTICS:
        ( A ) LENGTH: 30 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:11:

| Phe | Glu | Phe | Thr | Leu | Val | His | Cys | Pro | Asp | Leu | Met | Lys | Asp | Arg | His |
| --- | --- | --- | --- | --- | --- | --- | --- | --- | --- | --- | --- | --- | --- | --- | --- |
| 1   |     |     |     | 5   |     |     |     |     | 10  |     |     |     |     | 15  |     |
| Leu | Asp | Gln | Leu | Leu | Leu | Cys | Ala | Phe | Tyr | Ile | Met | Ala | Lys |
|     |     |     | 20  |     |     |     |     | 25  |     |     |     |     | 30  |

( 2 ) INFORMATION FOR SEQ ID NO:12:

( i ) SEQUENCE CHARACTERISTICS:
        ( A ) LENGTH: 21 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:12:

| Asp | Leu | Met | Lys | Asp | Arg | His | Leu | Asp | Gln | Leu | Leu | Leu | Cys | Ala | Phe |
| --- | --- | --- | --- | --- | --- | --- | --- | --- | --- | --- | --- | --- | --- | --- | --- |
| 1   |     |     |     | 5   |     |     |     |     | 10  |     |     |     |     | 15  |     |
| Tyr | Ile | Met | Ala | Lys |
|     |     |     | 20  |     |

( 2 ) INFORMATION FOR SEQ ID NO:13:

( i ) SEQUENCE CHARACTERISTICS:
        ( A ) LENGTH: 18 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:13:

| Lys | Asp | Arg | His | Leu | Asp | Gln | Leu | Leu | Leu | Cys | Ala | Phe | Tyr | Ile | Met |
| --- | --- | --- | --- | --- | --- | --- | --- | --- | --- | --- | --- | --- | --- | --- | --- |
| 1   |     |     |     | 5   |     |     |     |     | 10  |     |     |     |     | 15  |     |
| Ala | Lys |

( 2 ) INFORMATION FOR SEQ ID NO:14:

( i ) SEQUENCE CHARACTERISTICS:
        ( A ) LENGTH: 14 amino acids
        ( B ) TYPE: amino acid
        ( C ) STRANDEDNESS: single ( D ) TOPOLOGY: linear ( i i ) MOLECULE TYPE: peptide ( x i ) SEQUENCE DESCRIPTION: SEQ ID NO:14:

Leu Asp Gln Leu Leu Leu Cys Ala Phe Tyr Ile Met Ala Lys
1               5                           10

( 2 ) INFORMATION FOR SEQ ID NO:15:

( i ) SEQUENCE CHARACTERISTICS:
        ( A ) LENGTH: 7 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:15:

Ala Phe Tyr Ile Met Ala Lys
1               5

( 2 ) INFORMATION FOR SEQ ID NO:16:

( i ) SEQUENCE CHARACTERISTICS:
        ( A ) LENGTH: 5 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:16:

Tyr Ile Met Ala Lys
1               5

( 2 ) INFORMATION FOR SEQ ID NO:17:

( i ) SEQUENCE CHARACTERISTICS:
        ( A ) LENGTH: 7 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:17:

Leu Cys Ala Phe Tyr Ile Met
1               5

( 2 ) INFORMATION FOR SEQ ID NO:18:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:18:

Leu Cys Ala Phe Tyr Ile
1               5

( 2 ) INFORMATION FOR SEQ ID NO:19:

( i ) SEQUENCE CHARACTERISTICS:
        ( A ) LENGTH: 5 amino acids
        ( B ) TYPE: amino acid
        ( C ) STRANDEDNESS: single (D) TOPOLOGY: linear (ii) MOLECULE TYPE: peptide (xi) SEQUENCE DESCRIPTION: SEQ ID NO:19:

Leu  Cys  Ala  Phe  Tyr
        1                    5

(2) INFORMATION FOR SEQ ID NO:20:

(i) SEQUENCE CHARACTERISTICS:
                    (A) LENGTH: 4 amino acids
                    (B) TYPE: amino acid
                    (C) STRANDEDNESS: single
                    (D) TOPOLOGY: linear (ii) MOLECULE TYPE: peptide (xi) SEQUENCE DESCRIPTION: SEQ ID NO:20:

Cys  Ala  Phe  Tyr
        1

(2) INFORMATION FOR SEQ ID NO:21:

(i) SEQUENCE CHARACTERISTICS:
                    (A) LENGTH: 9 amino acids
                    (B) TYPE: amino acid
                    (C) STRANDEDNESS: single
                    (D) TOPOLOGY: linear (ii) MOLECULE TYPE: peptide (xi) SEQUENCE DESCRIPTION: SEQ ID NO:21:

Leu  Phe  Ala  Phe  Tyr  Ile  Met  Ala  Lys
        1                    5

(2) INFORMATION FOR SEQ ID NO:22:

(i) SEQUENCE CHARACTERISTICS:
                    (A) LENGTH: 9 amino acids
                    (B) TYPE: amino acid
                    (C) STRANDEDNESS: single
                    (D) TOPOLOGY: linear (ii) MOLECULE TYPE: peptide (xi) SEQUENCE DESCRIPTION: SEQ ID NO:22:

Leu  Cys  Glu  Phe  Tyr  Ile  Met  Ala  Lys
        1                    5

(2) INFORMATION FOR SEQ ID NO:23:

(i) SEQUENCE CHARACTERISTICS:
                    (A) LENGTH: 9 amino acids
                    (B) TYPE: amino acid
                    (C) STRANDEDNESS: single
                    (D) TOPOLOGY: linear (ii) MOLECULE TYPE: peptide (xi) SEQUENCE DESCRIPTION: SEQ ID NO:23:

Leu  Cys  Ala  Ala  Tyr  Ile  Met  Ala  Lys
        1                    5

(2) INFORMATION FOR SEQ ID NO:24:

(i) SEQUENCE CHARACTERISTICS:
                    (A) LENGTH: 9 amino acids
                    (B) TYPE: amino acid
                    (C) STRANDEDNESS: single (D) TOPOLOGY: linear (i i) MOLECULE TYPE: peptide (x i) SEQUENCE DESCRIPTION: SEQ ID NO:24:

```
Leu Cys Ala Lys Tyr Ile Met Ala Lys
1               5
```

(2) INFORMATION FOR SEQ ID NO:25:

(i) SEQUENCE CHARACTERISTICS:
       (A) LENGTH: 9 amino acids
       (B) TYPE: amino acid
       (C) STRANDEDNESS: single
       (D) TOPOLOGY: linear (i i) MOLECULE TYPE: peptide (x i) SEQUENCE DESCRIPTION: SEQ ID NO:25:

```
Leu Cys Ala Tyr Tyr Ile Met Ala Lys
1               5
```

(2) INFORMATION FOR SEQ ID NO:26:

(i) SEQUENCE CHARACTERISTICS:
       (A) LENGTH: 9 amino acids
       (B) TYPE: amino acid
       (C) STRANDEDNESS: single
       (D) TOPOLOGY: linear (i i) MOLECULE TYPE: peptide (x i) SEQUENCE DESCRIPTION: SEQ ID NO:26:

```
Leu Cys Ala Phe Ala Ile Met Ala Lys
1               5
```

(2) INFORMATION FOR SEQ ID NO:27:

(i) SEQUENCE CHARACTERISTICS:
       (A) LENGTH: 9 amino acids
       (B) TYPE: amino acid
       (C) STRANDEDNESS: single
       (D) TOPOLOGY: linear (i i) MOLECULE TYPE: peptide (x i) SEQUENCE DESCRIPTION: SEQ ID NO:27:

```
Leu Cys Ala Phe Phe Ile Met Ala Lys
1               5
```

(2) INFORMATION FOR SEQ ID NO:28:

(i) SEQUENCE CHARACTERISTICS:
       (A) LENGTH: 9 amino acids
       (B) TYPE: amino acid
       (C) STRANDEDNESS: single
       (D) TOPOLOGY: linear (i i) MOLECULE TYPE: peptide (x i) SEQUENCE DESCRIPTION: SEQ ID NO:28:

```
Leu Cys Ala Phe Tyr Lys Met Ala Lys
1               5
```

(2) INFORMATION FOR SEQ ID NO:29:

(i) SEQUENCE CHARACTERISTICS:
       (A) LENGTH: 9 amino acids
       (B) TYPE: amino acid
       (C) STRANDEDNESS: single ( D ) TOPOLOGY: linear ( i i ) MOLECULE TYPE: peptide ( x i ) SEQUENCE DESCRIPTION: SEQ ID NO:29:

Leu Cys Ala Phe Tyr Ile Met Gln Lys
1               5

( 2 ) INFORMATION FOR SEQ ID NO:30:

( i ) SEQUENCE CHARACTERISTICS:
        ( A ) LENGTH: 12 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:30:

Pro Lys Lys Lys Arg Lys Val Cys Ala Phe Tyr Ile
1               5                   10

( 2 ) INFORMATION FOR SEQ ID NO:31:

( i ) SEQUENCE CHARACTERISTICS:
        ( A ) LENGTH: 7 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:31:

Arg Arg Cys Ala Phe Tyr Ile
1               5

( 2 ) INFORMATION FOR SEQ ID NO:32:

( i ) SEQUENCE CHARACTERISTICS:
        ( A ) LENGTH: 8 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:32:

Arg Lys Arg Cys Ala Phe Tyr Ile
1               5

( 2 ) INFORMATION FOR SEQ ID NO:33:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:33:

Ser Pro Lys Lys Gly Cys Ala Phe Tyr Ile
1               5                   10

( 2 ) INFORMATION FOR SEQ ID NO:34:

( i ) SEQUENCE CHARACTERISTICS:
        ( A ) LENGTH: 10 amino acids
        ( B ) TYPE: amino acid
        ( C ) STRANDEDNESS: single (D) TOPOLOGY: linear (i i) MOLECULE TYPE: peptide (x i) SEQUENCE DESCRIPTION: SEQ ID NO:34:

Cys Ala Phe Tyr Ile Gly Ser Pro Lys Lys
1               5                   10